United States Patent [19]
Chang et al.

[11] Patent Number: 5,453,487
[45] Date of Patent: Sep. 26, 1995

[54] SOLID PHASE PEPTIDE SYNTHESIZER

[76] Inventors: Heng-Wei Chang, 1051 Hatteras Ct., Foster City, Calif. 94404; Dario M. Slavazza, 259 N. Capitol Ave., #240, San Jose, Calif. 95127

[21] Appl. No.: 365,885

[22] Filed: Dec. 29, 1994

Related U.S. Application Data

[62] Division of Ser. No. 112,893, Aug. 27, 1993, Pat. No. 5,380,495.

[51] Int. Cl.$^6$ ..................................................... C07K 1/04
[52] U.S. Cl. ............................................................. 530/334
[58] Field of Search .................... 436/55; 935/87, 935/88; 422/62, 81, 108, 116, 131, 134, 136; 530/333, 334

[56] References Cited

U.S. PATENT DOCUMENTS

| | | | |
|---|---|---|---|
| 3,557,077 | 1/1971 | Brunfeldt et al. | 935/88 |
| 3,647,390 | 3/1972 | Kubodera et al. | 422/116 |
| 3,715,190 | 2/1973 | Park et al. | 530/334 |
| 4,362,699 | 12/1982 | Verlander et al. | 422/131 |
| 4,668,476 | 5/1987 | Bridgham et al. | 422/62 |
| 4,746,490 | 5/1988 | Saneii | 422/62 |
| 4,748,002 | 5/1988 | Neimark et al. | 422/116 |
| 4,800,166 | 1/1989 | Horn et al. | 436/55 |
| 4,816,513 | 3/1989 | Bridgham et al. | 525/54.1 |
| 4,861,866 | 8/1989 | Durrum et al. | 530/333 |
| 5,026,773 | 6/1991 | Steel | 525/54.11 |
| 5,053,454 | 10/1991 | Judd | 525/54.11 |
| 5,186,898 | 2/1993 | Bridgham et al. | 422/102 |
| 5,223,435 | 6/1993 | Kohr | 436/89 |
| 5,240,680 | 8/1993 | Zuckerman et al. | 422/67 |
| 5,380,495 | 1/1995 | Chang et al. | 422/131 |

OTHER PUBLICATIONS

Stewart et al., "Solid Phase Peptide Synthesis", 2nd ed., published 1984 by Pierce Chemical Co., (Rockford, Ill.), pp. 130–133.

*Primary Examiner*—Jeffrey E. Russel
*Attorney, Agent, or Firm*—Flehr, Hohbach, Test, Albritton & Herbert; Richard Aron Osman

[57] ABSTRACT

The invention provides methods and apparatuses for solid-phase peptide synthesis which employ solvent/reagent delivery and measuring systems open to atmospheric pressure coupled to pressurized transfer and reaction systems. The delivery and measuring systems consists of multiple solvent vessels connected to a metering vessel through individual, uninterrupted solvent lines. The metering vessel is connected to a transfer vessel by a valve through which solvent is gravity fed to the transfer vessel. The solvent is now in a closed, single pathway system and can be pressurized from the transfer vessel to a reaction vessel. This closed system allows the complete inversion of the reaction vessel; with the advantage of guaranteeing complete resin to solvent contact without any possibility of loss of resin product. All of the steps are accomplished by the opening and closing of individual valves that are controlled through a personal computer and system software that allow the user to do these steps individually or in any combination and length.

1 Claim, 2 Drawing Sheets

5,453,487

SOLID PHASE PEPTIDE SYNTHESIZER

This is a division of application Ser. No. 08/112,893 filed Aug. 27, 1993, now U.S. Pat. No. 5,380,495.

FIELD OF THE INVENTION

The field of the invention is automated peptide synthesis.

BACKGROUND OF THE INVENTION

In 1962, R. B. Merrifield first reported a method for solid phase peptide synthesis (SPPS). One of the major advantages of this technique was the ability to automate the organic synthesis of peptides. However, a commercially viable automated SPPS instrument must efficiently accomplish solvent and reagent delivery, measurement and mixing with resin at the lowest possible cost. Unfortunately, the SPPS instruments produced to date suffer from a number of deficiencies and undesirable or costly compromises.

It is advantageous to be able to run direct, uninterrupted lines from the solvent and reagent supplies. This prevents common flow paths (a potential source of cross-contamination) and the need for intervening valves (which add substantial cost). However, in order to run-uninterrupted lines, the receiving vessel must be open to atmospheric pressure which places severe restrictions on the mixing operation and subsequent solvent flow.

One commercial instrument (Beckman Model 990) does provide uninterrupted lines that discharge into an open measuring vessel. Solvent is gravity fed therefrom into a conical reaction vessel. Since the reaction vessel cannot be tipped, mixing is accomplished by a mechanical stirring rod. This method provides mixing inferior to rocking or inverting mixing, suffers from resin getting stuck up on the sides of the reaction vessel, and introduces mechanical shear forces which may deleteriously impact nascent peptides, especially longer synthetic peptides.

The present invention provides an apparatus and method that creatively solves the prior art deficiencies, while allowing this single instrument to efficiently accommodate a wide variety of synthetic chemistries.

Cited Literature

For a review of SPPS and the chemistries involved, see John M. Stewart and Janice D. Young (1992) Solid-Phase Peptide Synthesis, Second Ed.

Recent patents directed to SPPS instruments and apparatuses include: Saneii (1988) U.S. Pat. No. 4,746,490, Bridgham et al (1987) U.S. Pat. No. 4,668,476, Bridgham et al (1989) U.S. Pat. No. 4,816,513 and Bridgham et al (1993) U.S. Pat. No. 5,186,898.

SUMMARY OF INVENTION

The solid-phase peptide synthesis apparatus and method disclosed herein employ solvent/reagent delivery and measuring systems open to atmospheric pressure coupled to pressurized transfer and reaction systems. The invention uses pressurized inert gas, preferably nitrogen, and an open system to allow all of the solvents, reagents and reactants, e.g. amino acids to be transferred using separate uninterrupted lines eliminating significant risks of cross-contamination. In a preferred embodiment, solvents and reagents are moved from the solvent containers to a metering vessel using nitrogen pressure. The metering vessel consists of a chamber with multiple photo-sensors for measuring the amount of solvent contained therein. The metering vessel is connected to a transfer vessel by a single valve through which solvent is gravity fed to the transfer vessel.

The solvent is now in a closed, single pathway system and can be pressurized from the transfer vessel to a reaction vessel. Thus, by going from an open measuring system to a closed single pathway transfer system, solvent is delivered to a reaction vessel that is sealed and filtered at both ends. This closed system allows the complete inversion of the reaction vessel; with the advantage of guaranteeing complete resin to solvent contact without any possibility of loss of resin product.

This combination of solvent transfer, solvent volume measurement, solvent combining and resin mixing does not limit the user in choices of synthesis strategies and allows an extremely wide range in synthesis scale. This combination is completely amenable to scale up, allowing peptide synthesis on a manufacturing scale. Because of the freedom to choose any synthesis strategy and the ability to scale-up, methods development and product manufacture is much more easily accomplished.

DETAILED DESCRIPTION OF THE INVENTION

The invention provides methods and apparatuses for solid-phase peptide synthesis which employ solvent/reagent/reactant (henceforth, "solvent") delivery and measuring systems open to atmospheric pressure coupled to pressurized transfer and reaction systems. The delivery and measuring systems consists of multiple solvent vessels connected to a metering vessel through individual, uninterrupted solvent lines.

Suitable solvent lines are selected on the basis of solvent compatibility, volume and flow-rate requirements, flexibility, durability, etc. Preferred materials include Teflon (polytetrafluoroethylene), polyethylene and polypropylene. A line may be any conduit capable of transferring solvent or gas such as piping and tubing, especially flexible Teflon (polytetrafluoroethylene) tubing. By uninterrupted is meant that the solvent need not pass through any valves nor shared solvent paths en route from the solvent to a metering vessel. Accordingly, valve use and exposure of potentially sensitive parts to corrosive or disruptive solvents, reagents, reactants and reaction conditions is mimimized. The solvents are conducted from the solvent vessel to the metering vessel by a pressure differential, generally produced by temporarily pressurizing the solvent vessel with a preferably dry and inert gas such as nitrogen. Accordingly, the solvent vessels are normally sealed except for ports to the source of pressurized gas and to the metering vessel.

Each solvent is transferred through an uninterrupted line to a metering vessel, though it is often convenient to employ a plurality of metering vessels to further segregate certain solvents. In a preferred embodiment, two metering vessels are used providing for separate metering of acidic and basic solvents. The metering vessel(s) preferably comprise means for detecting the volume of solvent therein in order to regulate volumes delivered to the transfer vessel and ultimately, the reaction vessel. Solvent volume may be detected by a variety of ways including vessel weight, float height, or preferably, a plurality of photo-sensors. The volume detection-means are generally electronically coupled to computational and display means to facilitate user control and monitoring.

In operation, a predetermined volume of solvent is generally gravity fed from the metering vessel(s) which is/are open to atmospheric or ambient pressure, through a valve to a transfer vessel capable of being isolated from atmospheric pressure. The transfer vessel is coupled to a source of pressurized gas and to a reaction vessel through separate valves. After delivery of solvent from the metering vessel(s), the solvent is directed under pressure into a reaction vessel. During transfer, a second valve coupled to an outlet port of the reaction vessel provides for venting to atmospheric pressure or displacement from the reaction vessel.

Figure 1:
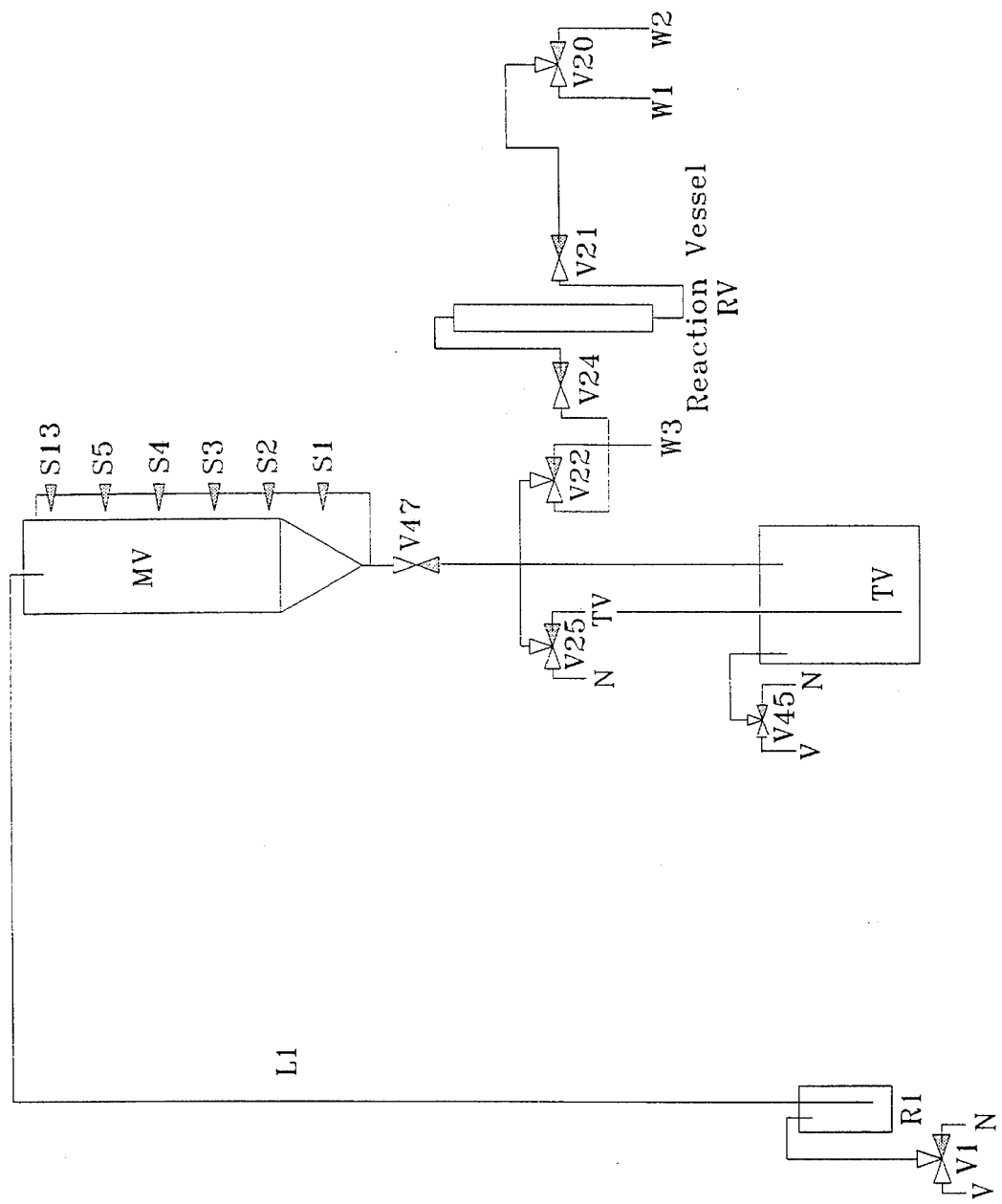
FIG. 1 shows an expanded view of the open to closed flow path. This schematic shows the basic components of the C S Bio peptide synthesizer.

FIG. 1 shows an expanded view of the open to closed flow path. This schematic shows the basic components of the C S Bio peptide synthesizer. The use of an unenumerated capital letter "V" or "N" at valve leads indicates the lead is directed to a vent or pressurized nitrogen gas, respectively. The solvent container (R1) is normally vented to the atmosphere through valve 1 (V1). When V1 is activated, nitrogen pressurizes R1 forcing solvent through uninterrupted solvent line (L1) to the metering vessel (MV). The solvent volume is measured with the photo-sensors (S1–S5) on the side of the metering vessel (MV). Sensor 13 (S13) is used as a safety overflow cutoff sensor. Solvent is dropped from the (MV) to the transfer vessel (TV) through valve 47 (V47). With V47 closed valve 45 (V45) can allow nitrogen to pressurize the TV to force solvent through valves 22, 24, and 25 (V22, V24, V25) to the reaction vessel (RV). The reaction vessel (RV) is filtered at both ends and is where the resin with the growing peptide is kept. The RV can be inverted 180 degrees back and forth to mix the resin and solvent. The solvent is removed from the RV with nitrogen pressure delivered through V25. The solvent leaves the RV through valves 20 and 21 (V20, V21). Valve 20 (V20) can be used to send the solvent from the RV to one of two places (W1 or W2). Valve 22 (V22) is used to send solvent from the TV to waste (W3) if desired, bypassing the RV. Valves 21 and 24 (V21, V24) are normally closed to keep solvent in the RV.

Figure 2:
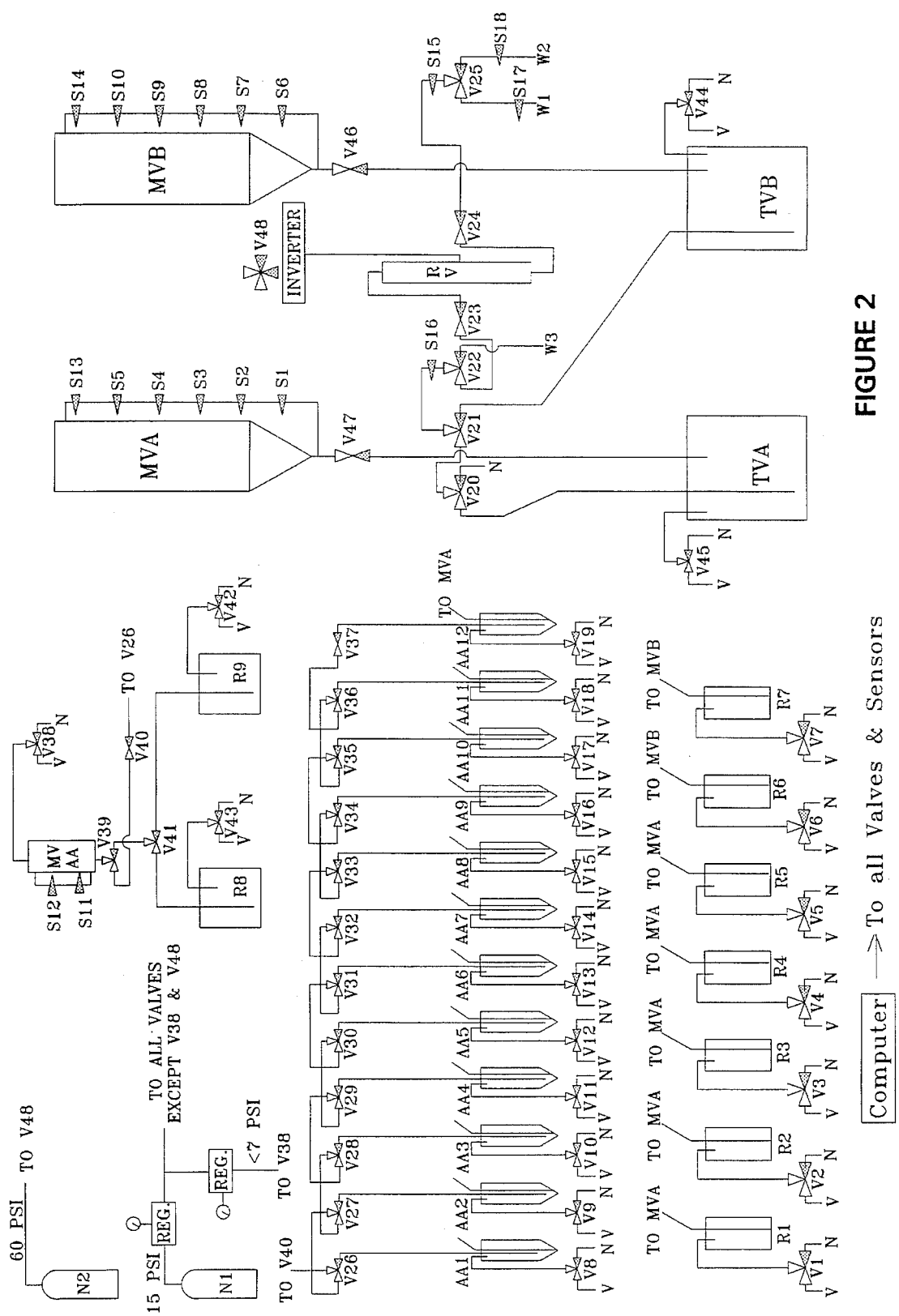
FIG. 2 shows a complete flow schematic of the C S Bio model 536 peptide synthesizer.

FIG. 2 shows a complete flow schematic of the C S Bio model 536 peptide synthesizer, with nine solvent reservoirs (R1–R9), twelve amino acid reservoirs (AA1–AA12), two metering vessels (MVA and MVB), two transfer vessels (TVA and TVB), one reaction vessel (RV), one amino acid metering vessel (MVAA), two nitrogen supplies (N1 and N2), eighteen photo-sensors (S1–S18) and forty eight valves (1–48).

The mixing of the reaction vessel (RV) is accomplished with a rotary actuator (not shown), a four-way valve (V48) and 60 psi of nitrogen from (N2). The line from (N2) is split and down-regulated to 15 psi for an oil reservoir which cushions the mixing motion. All other nitrogen comes from the (N1) supply. Solvent reservoirs 1–5 (R1–R5) contain solvents that can be delivered to (MVA). Solvent reservoirs 6–7 (R6–R7) contain solvents that can be delivered to (MVB).

Reagent volume is measured using photo-sensors 1–5 (S1–S5) in MVA and using photo-sensors 6–10 (S6–S10) in MVB. Photo-sensors 13 (S13) and 14 (S14) are both overflow cut-off sensors. Valves 1–7 (V1–7) deliver nitrogen to R1–R7 respectively, to cause the transfer of solvent from the solvent containers to the metering vessels.

Amino acid vials 1–12 (AA1–AA12) contain the amino acids which are to be used to synthesize the peptide. The dissolved amino acids in AA1–AA12 can be transferred independently, directly to MVA using nitrogen pressure from valves 8–19 (V8–19). Reagent is delivered to the amino acid vials (AA1–AA12) through a series of valves (V26–39), from the amino acid solvent metering vessel (MVAA). Reagent is delivered to the MVAA from reagent bottles 8 and 9 (R8, R9) using valves 38–43 (V38–43). Sensors 11 and 12 (S11, S12) are used to measure the correct volume of reagent needed for the amino acid vials.

Once reagent is in MVA or MVB it can be gravity fed to the respective transfer vessel (TVA, TVB) through valves 47 or 46 (V47, V46) respectively. Once reagent is in transfer vessel TVA or TVB, nitrogen pressure through valves 45 or 44 is used to send the reagent to the reaction vessel (RV) through valves 22–25 (V22–25). Sensor 16 (S16) is used to monitor the completion of this transfer. The reagent in the reaction vessel can be removed using nitrogen pressure through valve 25 (V25), sending reagent through 21 and 20. Sensor 15 (S15) is used to determine when this step is complete. Valve 24 (V24) and Valve 23 (V23) are used to let reagent in or out of the RV and also to hold reagent in the RV. Valve 20 (V20) is used to allow the choice of two reagent paths from the reaction vessel (RV). Sensor 17 (S17) and Sensor 18 (S18) can be used as waste container overflow detectors.

The reaction vessel is designed to be sealable, such that the vessel may be both pressurized and/or tipped or even inverted without loss or spillage of solvent or resin. The compatibility of the reaction vessel with pressurization is important to facilitate loading and evacuating the vessel— especially if the inlet and/or outlet valve is protected from the solid-phase resin by a filter. In a preferred embodiment, the reaction vessel permits single flow-path loading and evacuation, e.g. the two valves are coupled to ports proximal to opposite ends of the vessel's elongated axis and each valve is separated from the solid-phase resin contained by the vessel by a filter which transmits solvent but retains solid-phase resin. Thus, by providing pressurized transfer of solvent from the metering vessel, the present invention permits the use of fine-pore resin filters which would otherwise impractically restrict solvent transfer into and out from the reaction vessel.

The ability to tip the reaction vessel is also important. The reaction vessel provides the environment for chemical synthesis of the peptide on the solid phase, which synthesis is facilitated by thorough mixing. Because the reaction vessel may be tipped, the reaction vessel may be subject to a wide variety of motions to provide mixing, including shaking, rocking, rotating, etc. In a preferred embodiment, the reaction vessel is other than spherical, preferably elongated along one axis and mixing is provided by rotating (including rotational oscillation) the vessel on an axis at an angle to its elongated axis, where the angle is between 30 and 90 degrees, preferably between about 60 and 90, more preferably between about 75 and 90, most preferably about 90 degrees. In other words, in a most preferred embodiment, the reaction vessel is rotated on an axis orthogonal to its elongated axis.

The reaction vessel is preferably subject to oscillating as opposed to continual rotation, generally rotating through between 30 and 180 degrees, preferably between 60 and 180 degrees, more preferably between 90 and 180 degrees, and most preferably about 180 degrees (inverting) to promote full resin to solvent mixing.

After the reaction has been carried to the desired degree of completion, the solvent can then be removed from the reaction vessel using pressurized nitrogen.

All of the steps are accomplished by the opening and closing of individual valves that are controlled through a personal computer and system software that allow the user to do these steps individually or in any combination and length. A variety of valves may be used and actuated in a variety of ways compatible with peptide synthesis chemistry. In a preferred embodiment, teflon diaphram valves are actuated pneumatically or by solenoid.

Suitable vessels (solvent, metering, transfer, and reaction) are selected on the basis of chemical compatibility, volume and flow-rate requirements, stowability, compatibility with the selected volumetric detection means, etc., may be purchased from a variety of commercial vendors. Preferred vessel materials include glass, polypropylene and polyethylene. Glass is the most preferred material for the metering, transfer and reaction vessels.

Accordingly, the apparatuses and methods disclosed herein provide for automated solid-phase peptide synthesis with the combined advantages of uninterrupted solvent delivery lines and and an invertible reaction vessel.

The following examples are offered by way of illustration and not by way of limitation.

EXAMPLE

The principal components of the C S Bio Co. Peptide Synthesizer may be grouped into 4 systems:

1. Amino acid reservoirs: The amino acids used in the synthesis are contained in twelve (model 536) and twenty (model 136) individual tubes on the upper left side of the instrument.

2. Reagent reservoirs: The reagents and solvents are located in the left compartment. There are seven reagent bottles that deliver to the metering vessel(MV), and two reagent bottles that deliver to the AA metering vessel (MVAA).

3. Reaction chamber: The reaction chamber is located in the right side compartment and consists of two of metering vessels (MVA and MVB), two of transfer vessels (TVA and TVB) and a reaction vessel (RV).

4. Computer: This contains the program that controls the peptide synthesizer and allows control of all operations.

FUNCTIONS

The C S Bio peptide synthesizer performs twelve basic functions in response to programmed instructions. The operations are: Custom function, Transfer, Meter (Rx—MVX), Meter/Mix (Rx—MVX), Meter AAx, Meter/Mix AAx, Bubble AAx, Bubble/Mix AAx, Meter (Rx—MVAA), Pause, Drain, and Mix. These operations can be performed manually, (via the computer) or programmed to operate in any sequence without operator attention.

CUSTOM FUNCTION

This function allows the user to pre-select up to ten (custom) operations by defining individual valves that can be opened for a specific time. This is a timed function.

TRANSFER

Reagents must go from the metering vessel to the reaction vessel or waste container via the transfer vessel. Two transfer steps are employed: 1. metering vessel to transfer vessel (accomplished by gravity), 2. transfer vessel to reaction vessel or waste container (accomplished with nitrogen pressure). Both these transfer steps can be a timed or sensor function.

METER (Rx—MVX)

In the metering operation, nitrogen pressure is used to deliver a quantity of reagent from reagent bottles 1 to 5 (R1–R5) into metering vessel A (MVA) and reagent bottles 6–7 (R6–R7) into metering vessel B (MVB).

When reagents are metered, the volume of liquid is detected by the photoelectric sensors attached to the metering vessel. When the appropriate level is reached the reagent bottle is vented stopping the flow of reagent to the metering vessel. Within a pre-defined malfunction time, if the appropriate level is not reacted, the instrument will call for a malfunction and stop.

METER/MIX (Rx—MVX)

Time can be saved by using a meter/mix function. This function allows both the metering of reagents and the mixing of the reaction vessel to occur simultaneously.

METER (AAx)

This function allows the dissolved amino acid in the amino acid reservoir to be delivered to metering vessel A (MVA). This is a timed function.

METER/MIX (AAx)

This function allows the two functions Meter AAx and Mix to occur simultaneously.

BUBBLE (AAx)

This function allows the reagent in the amino acid metering vessel (MVAA) to be delivered to a specified amino acid reservoir and will, via nitrogen, bubble to dissolve the amino acid in the amino acid reservoir. This is a timed function.

BUBBLE/MIX (AAx)

This function allows the two functions Bubble AAx and Mix to occur simultaneously.

DRAIN

Draining of the reagent from the reaction vessel is accomplished by pressurizing the reaction vessel with nitrogen, forcing the reagent to the waste container.

MIX

Upon command, mixing begins and continues for a pre-determined length of time. Complete mixing is accomplished by 180 degree inversion of the reaction vessel. This is a timed function.

PAUSE

To hold the automatic synthesis until the user re-starts the synthesis.

METER (Rx—MVAA)

This function allows reagents to be transferred from solvent bottle 8 or 9 to the amino acid metering vessel (MVAA). The amount of reagent is determined by a photoelectric sensor on the amino acid metering vessel.

STRUCTURE

MAIN RESERVOIRS

There are seven main reservoirs in the main compartments that deliver reagents to the metering vessel. Reagents 1 to 5 deliver to metering vessel A and reagent 6 and 7 deliver to metering vessel B. Each reservoir has two lines, one pressure/vent, and one for reagent delivery.

AMINO ACID REAGENT RESERVOIRS

There are two reagent reservoirs (R8 and R9) that will deliver reagent to the amino acid vessels via the amino acid metering vessel (MVAA).

AMINO ACID METERING VESSEL (MVAA)

This metering vessel located inside the main compartment has two photoelectric sensors that can be manually adjusted to measure the desired volume of reagent from R8 or R9 that will be sent on to the amino acid vessels.

AMINO ACID RESERVOIRS

There are twelve 50 mL (model 536) or twenty 20 mL (model 136) amino acid reservoirs across the front of the main compartment. Amino acids can be dissolved in-situ and delivered by pressure to metering vessel A. The bubbling used to dissolve the amino acid can be adjusted manually using the regulator located on the left side of the instrument.

METERING VESSELS

There are two main metering vessels (MVA and MVB). MVA is used to meter reagent 1–5 and MVB is used to meter reagent 6–7.

Each metering vessel has five photoelectric sensors. These sensors are used to determine the volume of reagent needed. They can be manually adjusted. In addition each metering vessel is provided with an overflow photoelectric sensor that will shutdown the instrument in the event of a problem with any of the metering sensors. The instrument is also programmed to malfunction if a level sensor can not detect reagent within the preset malfunction time.

The dissolved amino acids are metered into MVA by time rather than using the level sensor, however the instrument is programmed to shut down in the event level sensor 1 does not detect reagent after the amino acid delivery time expires.

TRANSFER VESSEL

All of the reagents metered into the metering vessels are transferred into the transfer vessel (MVA to TVA or MVB to TVB). This is a timed function. Once the reagent is in the transfer vessel, it is transferred to the reaction vessel via nitrogen pressure. This transfer (TVA to RV) can be either a timed function or a sensor detected function. Reagents can also be transferred directly to the waste container (TVA to W or TVB to W), by-passing the reaction vessel.

REACTION VESSEL

The reaction vessel is made of glass with fittings and filters on the ends. The mixing is via 180 degree rotation ensuring complete resin contact with all reagents. During transfer of solvent from TVA to RV or TVB to RV, the reaction vessel is in the inverted position, filling is from the bottom while the RV vents from the top. During draining the RV is in the upright position and nitrogen pressure forces reagent from the reaction vessel to the waste container. The mixing is accomplished by a rotary actuator and a 4-way solenoid valve.

WASTE CONTAINER

The waste container holds 20 L. The top of the container is closed with a cap and insert bearing four lines, two lines from the reaction vessel, one line from the transfer vessels, and one exhaust line to be vented in a fume hood.

INSTRUMENT

The entire instrument container is made of welded polypropylene and is completely inert to any of the reagents used during peptide synthesis. It is also equipped with an exhaust blower that will maintain the main compartment at a slightly reduced pressure, the blower is to be vented to a fume hood.

SOFTWARE

The C S Bio peptide synthesizer software uses three main screens to operate the peptide synthesizer. All three screens can be reached from the overhead menu, they are "Manual", "Edit", and "Synthesis". The manual screen allows a user to call up any function and then immediately run that function. The edit screen allow a user to create synthesis protocols by calling up the functions then storing them in sequential order for use in the synthesis screen. The synthesis screen allows the synthesizer to perform functions fully automatically.

The overhead menu has four option in addition to "Edit", "Manual", and "Synthesis". They are "File", "Define", "Custom", and "Quit". The "File" option has five sub headings, "New", "Load", "Save", "Print", and "Type". "New" is used while in the edit screen to set up the operation menu for a new synthesis protocol. "Load" is used in the edit screen to load-up previously saved synthesis protocols and is used in the synthesis screen to load-up protocols. "Save" is used to save a just written synthesis protocol. "Print" is used to print-out a synthesis protocol or saved run log. "Type" is used to show on screen a synthesis protocol or saved run log. The "Define" option is used to set the default values (rotary time, malfunction time, transfer time, and drain time). The "Custom function" is used to pro-define the valves to be called up in the "Custom function" operation. The "Quit" option can be used to leave the C S Bio software.

MANUAL SCREEN

The synthesizer functions are run individually by the operator.

There are twelve basic functions that the model 536 synthesizer can be instructed to perform. Custom function #, Transfer, Meter (Rx—MVX), Meter/Mix (Rx—MVX), Meter (AAx—MVA), Meter/Mix (AAx—MVA), Bubble AAx, Bubble/Mix AAx, Drain, Mix, Pause, and Meter (Rx—MVAA). Some of these functions can be performed simultaneously such as Meter/Mix (Rx—MVX), Bubble/Mix AAx, . . . etc.

To use any of these operations, the operator clicks once on "Manual" from the overhead menu. This takes you to the "Manual Screen". A list of functions will display.

Custom function: This function allows the user to select up to four valves, that can be opened for a selected amount of time. Up to ten different custom functions may be called in this function. Users have to pre-define the valve numbers at the "Custom" overhead option.
Step 1: Click on "Custom" overhead option and enter the desired valve numbers for the custom function.
Step 2: Click on "Custom function #X".
Step 3: Click on the desired "Custom function number".
Step 4: Click on the time and enter the time.
Step 5: Click on "Run".

Transfer: There are six transfers of solvent that can be called up under this function.

1) MVA to TVA, in which solvent is transferred from metering vessel A to transfer vessel A.

2) MVB to TVB, in which solvent is transferred from metering vessel B to transfer vessel B. Both MVA to TVA and MVB to TVB functions will normally be run automatically after a meter or meter/mix function is complete. MVA to TVA is two steps, a: Sensor 1 waits until it sees no more solvent, b: the operation is complete at a pre-defined transfer time. This pre-defined time is set in the overhead "Define" option under "Transfer Time". MVB to TVB works the same way except sensor 6 is used to look for solvent.

3) TVA to RV and

4) TVB to RV, both of these functions send solvent from the transfer vessel A or B to the reaction vessel. Completion of this function is normally determined by sensor 16, but by setting the sensor to 0 time will determine when the transfer is complete. If sensor 16 is used the function is done in three steps. a. The sensor looks to see solvent. b. The sensor waits until it does not see solvent. c. The transfer is complete at a pre-defined time after the sensor sees no solvent. The pre-define time is the "Transfer Time" previously set for 1 and 2.

5) TVA to W and

6) TVB to W are used to transfer solvent from the transfer vessel to the waste (by-passing the reaction vessel). TVA to W and TVB to W also normally use sensor 16 to determine completion but can use time by entering 0 for the sensor. If the sensor is used then TVA to W or TVB to W works the same as TVA to RV or TVB to RV.
Step 1; Click on "Transfer MVA to TVA".
Step 2: Click on the desired function (MVA to TVA, MVB to TVB, TVA to RV, TVB to RV, TVA to W, or TVB to W).
Step 3: Click on "Run" if you want the transfer function to use the sensor, or enter the sensor number to 0 and enter the desired time for the transfer then click on "Run".

Meter (Rx—MVX): There are seven solvent bottles to chose from. Solvents 1 to 5 (R1, R2, R3, R4, R5) meter into metering vessel A (MVA), solvent 1 (R1) has a shower head in the center. Solvent 6 to 7 (R6, R7) meter into metering vessel B (MVB), solvent 7 (R7) has a shower head in the center. After clicking "Meter Rx", the software will ask "which solvent" then will ask "which sensor level" then will return to the manual screen where you can see the function you have loaded. Click on "Run" to start the operation, when complete the operation will stop automatically or click on the "Stop" to end the operation early. The "Pause" will stop the operation but allows the operator to restart at the same place when "Run" is clicked again. After metering is complete, the solvent will transfer to the transfer vessel automatically. If the selected sensor does not detect solvent within the malfunction time, the instrument will stop and show a malfunction screen.
Step 1: Click on "Meter (Rx—MVA)".
Step 2: Click on the desired solvent "Meter R1—MVA", "Meter R2—MVA", "Meter R3—MVA", "Meter R4—TVA", "Meter R5—MVA", "Meter R6—MVB", or "Meter R7—MVB".
Step 3: Click on the desired sensor level and OK.
Step 4: Click on the desired time to call malfunction in case the solvent does not reach the desired sensor level.
Step 5: Click on "Run".

Meter/Mix (Rx—MVX): Time can be saved by using a meter/mix function. The metering malfunction time is pre-defined (at "Define Time" of the "Mal'ft Time") in case there is not solvent at the sensor level.
Step 1: Click on "Meter/Mix (Rx—MVA)".
Step 2: Click on the desired function "Meter/Mix (R1—MVA)", "Meter/Mix (R2—MVA)", "Meter/Mix (R3—MVA)", "Meter/Mix (R4—MVA)", "Meter/Mix (R5—MVA)", "Meter/Mix (R6—MVB)", or "Meter/Mix (R7—MVB)".
Step 3: Click on the desired sensor level and OK.
Step 4: Click on the desired time for "Mix".
Step 5: Click on "Run".

Meter (AAx—MVA): A time must be selected for this function. At the end of the selected time, the synthesizer will check sensor level 1 to determine if the amino acid has been delivered.
Step 1: Click on "Meter (AAx—MVA)".
Step 2: Click on the desired AA.
Step 3: Enter the desired time.
Step 4: Click on "Run".

Meter/Mix (AAx—MVA): The instrument will meter amino acid from amino acid reservoirs and mix simultaneously for the desired length of time.
Step 1: Click on "Meter/Mix (AAx—MVA)".
Step 2: Click on the desired AA.
Step 3: Enter the desired time for meter amino acid and mix.
Step 4: Click on "Run".

Bubble AAx: Taking the solvent from the amino acid metering vessel to the proper amino acid reservoir and dissolving the amino acid are both accomplished by selecting bubble amino acid.
Step 1: Click on "Bubble AAx".
Step 2: Click on the desired AA.
Step 3: Enter the desired time.
Step 4: Click on "Run".

Bubble/Mix AAx: Allows the dissolution of the amino acid and the mixing of the reaction vessel to occur simultaneously.
Step 1: Click on "Bubble/Mix AAx".
Step 2: Click on the desired AA.
Step 3: Enter the desired time.
Step 4: Click on "Run".

Drain: Drain can be a timed function or sensor function. Enter sensor number to 0 and enter the desired time for drain to be a timed function. The sensor function has three steps that are the same as the transfer function "TVA to RV".
Step 1: Click on "Drain 1".
Step 2: Click on "Drain 1" or "Drain 2".
Step 3: Click on "Run" for the sensor function or enter sensor number to 0 and enter the desired time for drain then click on "Run" for the timed function.

Mix:
Step 1: Click on "Mix".
Step 2: Click on "Mix" again and enter time.
Step 3: Click on "Run" to start.

Pause:
Step 1: Click on "Pause".
Step 2: Click on "Pause".
Step 3: Click on "Run".

Meter (Rx—MVAA): This function meters solvent from R8 or R9 to the MVAA.
Step 1: Click on "Meter Rx—MVAA".

Step 2: Click on "Meter R8—MVAA" or "Meter R9—MVAA".
Step 3: Click on the sensor level 11 or 12 then click on OK.
Step 4: Click on "Run".

EDIT SCREEN

The next main screen "Edit" is also selected from the above menu. This screen will not normally be used when operating the peptide synthesizer. Once your desired synthesis protocols are installed, most of the work will be in the synthesis screen or manual screen. The edit screen is where you will create the protocols that you will use to synthesize your peptide. This screen is identical to the manual screen and operates in exactly the same manner except that once a function is selected, the "Append" menu loads that function in step-wise fashion. The "Replace" menu, rather than adding the selected function next in line will replace the highlighted function. The "Insert" menu will insert the selected function behind the highlighted step. The "Delete" menu will erase the highlighted step. The loop-repeat will allow the operator to save some time in writing the protocols, if the operator wants to repeat a sequence of functions (steps). For example: If three steps need to be run four times (1 run, 3 repeats, total 4), then at the first step under loop enter 2 and under repeat enter 3. The 2 under the loop indicates that the first step plus the next 2 steps (total 3 steps) are in the loop. The 3 under repeat indicates that the loop will be run once then repeat 3 times (total 4 times).

When writing protocols, the operator must always remember:

1: To enter the desired TIME on the functions that require a timed operation such as "Custom function #", "Meter/Mix (Rx—MVA)", "Meter AAx", "Meter/Mix (AAx—MVA)", "Bubble AAx", "Bubble/Mix (AAx—MVA)", and "Mix". Also remember to click on "Append", "Insert", or "Replace" to load each function.
2: Use "Replace" to load the first step.
3: Click on any amino acid reservoir for "Meter AAx", "Meter/Mix AAx", "Bubble AAx", or "Bubble/Mix AAx". The amino acid reservoir number will depend upon the "Synthesis Screen" amino acid number during the synthesis.

SYNTHESIS SCREEN

The synthesis screen is where you will do fully automatic peptide synthesis. This screen shows twelve amino acid selections. This is where you can load the synthesis protocols that were created in the edit screen. The 12 amino acid selections correspond to the 12 amino acid vessels and each one can be run with its own synthesis protocols.

There are two ways to load synthesis protocols:
1: Click on the individual AA red box which will display the directory of stored protocols, and then select the desired protocol.
2. Click on "File" function from the overhead menu and select the "Load", now choose the desired protocol then click on "Enter" until you are done then click on "Cancel".

Once the protocols are loaded, remember to select the amino acid number you wish to start from and the amino acid number you wish to end at.

Step 1: Click on Start "AA#" and End "AA#".
Step 2: Click on "Start" to load the first amino acid protocol you want to start.
Step 3: Click on "Start" to start from the first step or double-click on any highlighted step to start from that step.

START UP

To run a peptide synthesis:
1. Power up the computer, monitor, and synthesizer.
2. Turn on the nitrogen pressure inlet to 60 psi.
3. Fill all the solvent reservoirs that will be used in the synthesis with proper solvents (empty-rinse and replace old solvents if necessary).
4. Add synthesis resin to proper size reaction vessel.
5. Add amino acids into the amino acid reservoirs.
6. Go to synthesis screen, select synthesis protocols for each amino acid.
7. Select starting AA and ending AA.
8. Click on "Start" to load the first amino acid protocol then on "Start" again to start the synthesis or double click on the highlighted step to start from that step.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of solid-phase peptide synthesis comprising steps:

(1) transferring by pressurized gas an organic solution comprising a selected activated amino acid composition through an uninterrupted solvent line to a metering vessel open to atmospheric pressure;

(2) metering by gravity flow a predetermined amount of said solution from said metering vessel through a first valve to a transfer vessel;

(3) transferring by pressurized gas a predetermined amount of said solution from said transfer vessel though a second valve to a reaction vessel containing solid phase;

(4) providing to said reaction vessel reagents to facilitate the chemical coupling of said amino acid composition to said solid phase;

(5) inverting said reaction vessel to chemically couple a portion of said amino acid composition to said solid phase; then (6) removing by pressurized gas the resultant amino acid depleted solution from said reaction vessel through a third valve.

* * * * *